United States Patent
White

(10) Patent No.: US 8,894,387 B2
(45) Date of Patent: Nov. 25, 2014

(54) HYDRODYNAMIC CHAMFER THRUST BEARING

(75) Inventor: Daniel G. White, Folsom, CA (US)

(73) Assignee: HeartWare, Inc., Miami Lakes, FL (US)

( * ) Notice: Subject to any disclaimer, the term of this patent is extended or adjusted under 35 U.S.C. 154(b) by 237 days.

(21) Appl. No.: 13/163,253

(22) Filed: Jun. 17, 2011

(65) Prior Publication Data

US 2011/0311383 A1 Dec. 22, 2011

Related U.S. Application Data

(60) Provisional application No. 61/397,972, filed on Jun. 18, 2010.

(51) Int. Cl.
F04B 17/03 (2006.01)
F04D 29/041 (2006.01)
F04D 29/18 (2006.01)
A61M 1/10 (2006.01)

(52) U.S. Cl.
CPC .......... *F04D 29/0413* (2013.01); *F04D 29/181* (2013.01); *A61M 1/101* (2013.01); *A61M 1/1017* (2014.02); *Y10S 415/90* (2013.01)
USPC ...... 417/353; 417/365; 417/423.12; 415/104; 415/900; 416/146 R; 416/174; 600/16

(58) Field of Classification Search
CPC . F04D 29/181; F04D 29/046; F04D 29/0413; F04D 29/0476; F04D 25/026; F04D 25/0606; F04D 25/064; F04D 25/06; F04D 3/005; F04D 3/02
USPC ......... 417/348, 352–354, 365, 423.1, 423.12; 415/104, 900; 416/146 R, 174; 600/16
See application file for complete search history.

(56) References Cited

U.S. PATENT DOCUMENTS

| 5,211,546 A * | 5/1993 | Isaacson et al. ............... 417/356 |
| 5,441,535 A | 8/1995 | Takahashi et al. |
| 6,752,602 B2 | 6/2004 | Schulte Eistrup et al. |
| 7,798,952 B2 * | 9/2010 | Tansley et al. .................. 600/16 |
| 7,997,854 B2 * | 8/2011 | Larose et al. ................. 415/106 |
| 8,551,163 B2 * | 10/2013 | Aber et al. .................... 623/3.14 |
| 2007/0100196 A1 * | 5/2007 | LaRose et al. .................. 600/16 |
| 2009/0112312 A1 | 4/2009 | LaRose et al. |
| 2009/0203957 A1 | 8/2009 | LaRose et al. |

OTHER PUBLICATIONS

International Preliminary Report on Patentability issued by the International Bureau of WIPO on Dec. 19, 2012 in connection with International Application No. PCT/US2011/040938.

(Continued)

*Primary Examiner* — Bryan Lettman
*Assistant Examiner* — Charles W Nichols
(74) *Attorney, Agent, or Firm* — Lerner, David, Littenberg, Krumholz & Mentlik, LLP

(57) ABSTRACT

An axial flow pump for a blood circulating pump for the circulation of blood, the rotor the rotor being constructed and arranged to impel blood in a downstream direction upon rotation of the rotor about its axis in a forward circumferential direction. The rotor is provided with hydrodynamic thrust bearing surfaces, each such thrust bearing surface being constructed and arranged to apply a hydrodynamic force to the rotor with a component of the force in the downstream direction upon rotation of the rotor in the forward circumferential direction.

16 Claims, 5 Drawing Sheets

(56) References Cited

OTHER PUBLICATIONS

Written Opinion of the International Searching Authority issued by the International Searching Authority (ISA/US) on Oct. 31, 2011 in connection with International Application No. PCT/US2011/040938.

International Search Report issued by the International Searching Authority (ISA/US) on Oct. 31, 2011 in connection with International Application No. PCT/US2011/040938.

* cited by examiner

HYDRODYNAMIC CHAMFER THRUST BEARING

This application claims the benefit of U.S. Provisional Application No. 61/397,972, filed Jun. 18, 2010, the contents of which are hereby incorporated by reference into this application.

BACKGROUND OF THE INVENTION

Heart pumps are typically used in the later stages of heart disease or after trauma to the heart, when the heart itself is too weak or otherwise incapable of creating sufficient blood pressure and blood circulation to satisfy body function.

Various heart pumps are already in use for the purpose of augmenting or replacing the blood pumping action of damaged or diseased hearts. Heart pumps are commonly used in three situations: (1) for acute support during cardio-pulmonary operations; (2) for short-term support while awaiting recovery of the heart from surgery; or (3) as a bridge to keep a patient alive while awaiting heart transplantation. The pumps may be designed to provide at least one of right or left ventricular assist, although left ventricular assist is the most common application in that it is far more common for the left ventricle to become diseased or damaged than it is for the right ventricle.

Intravascular pumps comprise miniaturized pumps capable of being percutaneously or surgically introduced into the vascular system of a patient, typically to provide left or right heart support, or even total heart support. Various types of intravascular pumps include radial flow centrifugal pumps and axial flow pumps. One form of axial flow heart pump is disclosed in co-pending, commonly assigned U.S. patent application Ser. No. 12/322,746 ("the '746 application"), the disclosure of which is hereby incorporated by reference herein. An axial flow pump according to certain embodiments of the '746 application uses magnetic or electromagnetic forces, for example, to power a magnetic rotor placed within a flow path of blood moving into or out of the heart. An electromagnet, or stator, is positioned around the outside of a tubular casing containing the flow path, whereas the rotor is disposed inside the casing. The axis of the rotor is coincident with the axis of the casing.

The rotor is magnetic. The stator typically is a set of electrically conductive coils. The rotor is energized by a power source with alternating currents through the coils to create a rotating magnetic field. That is, the field is directed transverse to the axis of the tubular casing, and the direction of the field rotates about the axis of the casing. As the field rotates, the rotor spins about its axis. The rotor is configured with vanes which impel the blood in a downstream direction along the axis as the rotor turns in a forward direction of rotation. The circumferential surface of the rotor includes hydrodynamic bearing surfaces. As the rotor turns, these surfaces generate radial forces which hold the rotor radially centered in the casing and out of contact with the wall of the casing. The magnetic field of the stator tends to keep the rotor at a fixed axial position, in alignment with the stator. This effect is commonly referred to as the "axial stiffness" of the stator. The power source may be implanted somewhere within the body of the patient or may be external to the patient, as is known in the art.

Axial flow cardiac pumps are efficient, compact and reliable. However, the forces associated with axial flow cardiac pumps can present problems. As the rotor impels the blood in the downstream direction, the blood applies thrust forces to the rotor. These thrust forces urge the rotor in the upstream direction. Moreover, the static pressure of the blood downstream from the rotor is greater than the static pressure of the blood upstream from the rotor. The pressure differential also urges the rotor in the upstream direction along the axis. Under certain flow conditions, especially at lower flow volumes and/or higher rotational speeds, the axial stiffness of the stator may not be capable of counteracting the axial forces on the rotor. In this case, the rotor may even contact a mechanical stop, such as a narrowed portion of the casing, which is provided as a backup or emergency restraint. Such contact can cause wear on the rotor and casing, which in turn can shorten the life of the pump and cause other undesirable effects.

BRIEF SUMMARY OF THE INVENTION

One aspect of the invention provides a rotor for a blood circulating pump. The rotor desirably has a magnetic, biocompatible body having an upstream end, a downstream end and an axis extending between the ends. The body desirably includes a plurality of vanes defining a plurality of channels therebetween, and is constructed and arranged to impel blood downstream upon rotation of said rotor in a forward circumferential direction. The vanes have hydrodynamic thrust bearing surfaces, each such thrust bearing surface being constructed and arranged to apply a hydrodynamic force to the rotor upon rotation of said rotor in the forward circumferential direction, with a component of this force directed in the downstream direction.

A further aspect of the invention provides an implantable blood circulating pump. The pump according to this aspect of the invention desirably includes a casing having an interior bore having an axis, an upstream end, a downstream end, and a stop surface bounding the bore. The said stop surface desirably is substantially in the form of at least a portion of a surface of revolution about the bore axis. Desirably, the stop surface has a diameter increasing progressively in a downstream direction along said bore axis. The pump according to this aspect of the invention desirably also includes a rotor disposed within the bore, the rotor comprising a magnetic, biocompatible body including a plurality of vanes defining a plurality of channels therebetween. Here again, the rotor constructed and arranged to impel blood downstream upon rotation of the rotor within said bore in a forward circumferential direction about the axis. In this embodiment as well, the vanes desirably have hydrodynamic thrust bearing surfaces, each such thrust bearing surface being constructed and arranged to apply a hydrodynamic force to said rotor with a component of said force in the downstream direction upon rotation of said rotor in the forward circumferential direction. The pump according to this aspect of the invention desirably also includes a stator disposed in proximity to the casing outside said bore, said stator including one or more electromagnetic coils for applying a magnetic field to said rotor so as to rotate said rotor about said axis.

As further explained below, the downstream forces applied to the rotor through the hydrodynamic thrust bearing surfaces helps to offset the forces tending to move the rotor upstream during operation.

DETAILED DESCRIPTION

Figure 1:
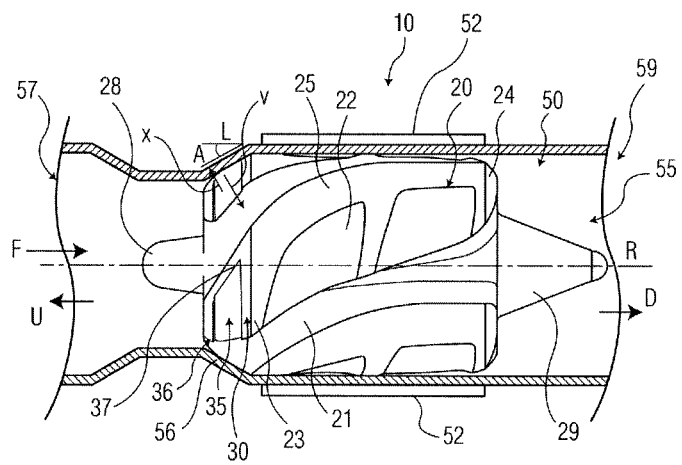
FIG. 1 is a diagrammatic section view depicting one embodiment of a blood circulating pump according to one embodiment of the invention.
Figure 2:
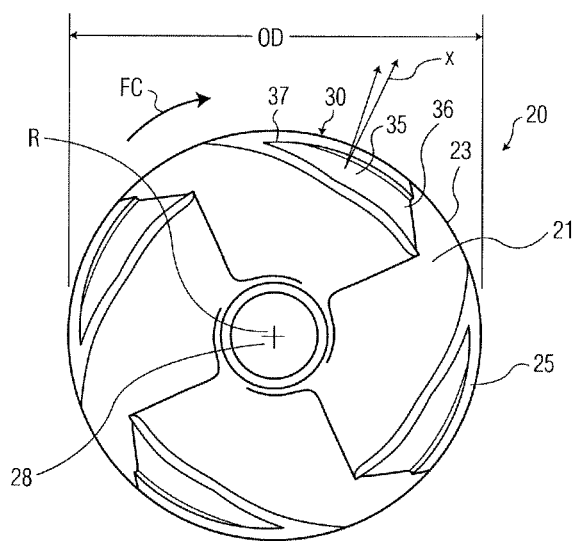
FIG. 2 is a front elevational view of a rotor used in the pump of FIG. 1.
Figure 3:
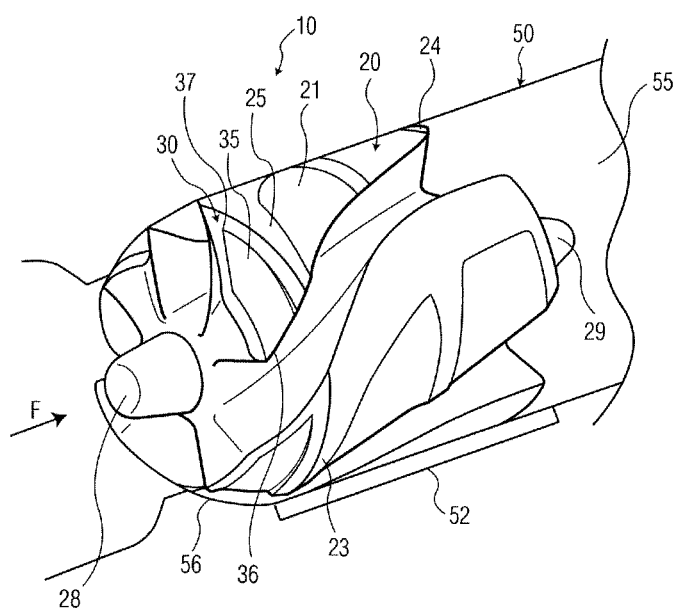
FIG. 3 is a diagrammatic, perspective view of the pump of FIG. 1, with certain elements depicted as transparent for clarity of illustration.

A blood circulating pump 10 according to first embodiment of the present invention, illustrated in FIGS. 1-3, includes a rotor having body 20. The body 20 is magnetic and biocompatible, and further includes an upstream end 23, a downstream end 24 and an axis R extending between the ends. The body 20 further includes a plurality of vanes 25 defining a plurality of channels 21 therebetween. The rotor body 20 is constructed and arranged to impel blood downstream, in the direction of fluid flow F, upon rotation of the rotor about axis R in a forward circumferential direction FC (FIG. 2). In the particular embodiment depicted, the forward circumferential direction FC is the clockwise direction as seen in FIG. 2, looking downstream towards the upstream end of the rotor.

Each vane 25 includes at least one hydrodynamic thrust bearing surface 35. As further explained below, each thrust bearing surface 35 is constructed and arranged to apply a hydrodynamic force V (FIG. 1) to the rotor with a component of the force in the downstream direction D upon rotation of the rotor in the forward circumferential direction FC. Each vane 25 also has additional radial bearing surfaces 22 along the length of body 20. The radial bearing surfaces are arranged to apply hydrodynamic forces directed generally radially inwardly, toward axis R, upon rotation of the rotor in the forward circumferential direction.

Each thrust bearing surface 35 has a normal vector X. As referred to herein, the normal vector of a surface is the vector directed out of the surface and perpendicular to the surface. Where the surface is non-planar, the normal vector of the surface as referred to herein should be understood as the integral of the normal vector over the entire extent of the surface. In the embodiment of FIGS. 1-3, the normal vector X of each thrust bearing surface includes non-zero components in the radially outward direction, in the upstream direction, and in the circumferentially forward direction. As best seen in FIG. 1, vector X projects in the upstream direction U and projects radially outward, away from the axis of rotation R. As best seen in FIG. 2, each vector X also slopes and slightly in the circumferentially forward direction.

Further in this embodiment, the rotor body 20 includes a principal surface of revolution about the axis R, generally defined as the peripheral surfaces of vanes 25, that is substantially cylindrical in shape. The substantially cylindrical principal surface of revolution generally has an outside diameter OD (FIG. 2), which is preferably about 4 to about 12 mm in the case of a blood pump intended for intravascular implantation in an adult human, and more preferably about 9 to 11 mm. Vanes 25 define chamfer surfaces 30 at the upstream ends of the vanes. The chamfer surfaces 30 slope radially outwardly in the downstream direction, so that the chamfer surfaces are generally in the form of portions of a conical surface of revolution about the axis having increasing diameter in the downstream direction. As illustrated in FIGS. 1-3, the downstream diameter of the chamfer surfaces 30 is substantially equal to the first diameter of the vanes and the cylindrical surface of revolution of body 20. Thrust bearing surfaces 35 are provided as portions of the chamfer surfaces 30. Thrust bearing surfaces 35 are recessed relative to surrounding portions of the chamfer surfaces 30 such that each thrust bearing surface 35 defines a pocket in the chamfer surfaces 30. Each pocket, defining thrust bearing surface 35, includes a leading portion 36 and a trailing portion 37, relative to the forward circumferential direction FC. The pocket has a progressively increasing depth such that the deepest portion of the pocket is at leading portion 36. Stated another way, each thrust bearing surface slopes progressively outward, toward the surrounding chamfer surface 30, in the direction from the leading portion to the trailing portion. Moreover, the leading portion 36 is open to adjacent channel 21. The difference between the thrust bearing surface 35 at leading portion 36 and the chamfered surface 30, measured adjacent to leading portion 36, defines a radial gap height, which may be within the range of about 0.0010 inches to about 0.0020 inches, such as, for example, 0.0010 inches, 0.0015 inches, 0.0020 inches, or the like.

As shown in FIG. 1, the chamfer surfaces 30 define a chamfer angle A such that the chamfer surfaces are positioned at an angle relative to axis R and relative the generally cylindrical surface of revolution of the rotor body 20. Chamfer angle desirably is in the range of about 20 degrees to about 45 degrees, and typically is less than 45 degrees. For example, the chamfer angle A of the chamfer surfaces 30 may be about 30 degrees. The chamfer surfaces 30 have a chamfer length L measured in the axial directions which may be in the range of about 0.06 inches (1.5 mm) to about 0.1 inches (2.5 mm). In one example, the chamfer length L is about 0.08 inches (2 mm).

The rotor body 20 may further include and projection members 28 and 29 extending upstream and downstream from the vanes. The particular example of the rotor shown in FIGS. 1-3 includes four vanes 25 defining four channels 21, each vane having two radial bearings 22 on the peripheral surfaces of the vanes defining the cylindrical surface of revolution of body 20. The configuration of the vanes, channels and radial thrust bearings may be generally in accordance with the aforementioned '746 application. Briefly, each channel 21 slopes in the circumferentially forward direction FC toward the upstream end of the body, so that as the body rotates in the circumferentially forward direction, the surfaces of the body defining the channels will impel blood in the downstream direction D. Each radial bearing 22 is formed as a recessed pocket in the peripheral surface of the vane, and each such pocket has its maximum depth at the leading edge of the pocket, i.e., the edge of the pocket which lies at the circumferentially forward side. The depth of each pocket 22 decreases progressively toward the trailing end of the pocket. The radial bearing pockets 22 are open to channels 21 at the leading edges of the pockets. Any number of vanes and radial bearings is contemplated.

Rotor body 20 is positioned within a hollow casing 50. The hollow casing 50 defines an interior bore 55 therethrough, within which the rotor body 20 is positioned. Casing 50 also includes an upstream end and a downstream end, corresponding to the direction of fluid flow F, and corresponding to the upstream and downstream ends of the rotor. The interior bore has a central axis R coincident with the central axis of the rotor, an inlet 57 at its upstream end and an outlet 59 at its downstream end. Casing 50 further includes a mechanical stop surface 56 positioned upstream of vanes and chamfer surfaces of rotor body 20. The stop surface 56 is intended to prohibit excessive upstream motion of the rotor body 20 out of its ordinary position.

As shown in FIG. 1, the stop surface 56 is positioned adjacent to a portion of the rotor body 20 and may be shaped similarly to such portion of body 20. In this embodiment, the stop surface 56 is substantially in the form of a surface of revolution about the central axis R, such surface facing inwardly toward the central axis. The stop surface 56 has a diameter increasing progressively in the downstream direction. In this embodiment, the stop surface 56 is substantially conical, and lies at an angle A to the central axis which is substantially equal to the angle A of the chamfer surfaces 30. The stop surface may have a length in the axial direction approximately equal to the length L of the chamfer surfaces 30. The smaller (minor) inside diameter of the stop surface should be less than the outside diameter OD defined by the vanes. The main portion of the bore 55, downstream from stop surface 56, desirably has an inside diameter just slightly larger than the outside diameter OD defined by the vanes on the rotor.

The casing may include additional features such as a downstream stop (not shown) to prevent movement of the rotor out of the casing through the outlet 59 while the pump is inactive. Also, a set of stationary vanes, sometimes referred to as a "diffuser" (not shown) may be positioned downstream from the rotor. The vanes of the diffuser may be arranged to reduce rotation of fluid around the axis R.

A stator 52 is disposed in proximity to casing 50 and outside of the interior bore 55 and preferably surrounding at least a portion of the rotor body 20. The stator 52 may include one or more electromagnetic coils, most commonly a plurality of coils such as three coils disposed at equal 120 degree intervals about the central axis R, as discussed above and as is known in the art. In operation, a power source (not shown) creates alternating currents which pass through the coils, to create a magnetic field in a direction transverse to axis R and rotating axis R. This field is applied to the rotor so as to rotate the rotor body 20 about axis R. The magnetic field of the stator also tends to hold the rotor in position along the axis, in alignment with the stator. As discussed above, this effect is referred to as the axial magnetic stiffness of the stator.

Casing 50 may be made of any non-ferromagnetic material capable of handling the rotor 20 operation, which substantially resists thrombosis, and which is biocompatible. Desirably, the casing material should be resistant to mechanical wear. For example, the material of casing 50 may be a ceramic. Rotor body 20 includes a magnetically hard ferromagnetic material, i.e., a material which forms a strong permanent magnet and which is resistant to demagnetization. The material of the rotor body also should be biocompatible and substantially non-thrombogenic. For example, the rotor body may be formed as a unitary mass of an alloy of platinum and cobalt. In other embodiments, the rotor body may be formed from a magnetic metal such as an iron-nickel alloy with an exterior coating of another material to increase the body's biocompatibility. The rotor is magnetized with a magnetic field transverse to the axis R, so as to provide magnetic poles at the peripheral surfaces of the vanes.

In operation, the pump is implanted in a mammalian subject such as a human subject, with the inlet 57 and outlet 59 of the bore in communication with the circulatory system of the subject. For example, if the pump is used to assist the left ventricle, the inlet 57 may be in communication with the interior of the left ventricle, whereas the outlet 59 may be in communication with the aorta. The stator is actuated by the power source to provide a rotating magnetic field and thus spin the rotor 20 about axis R in the forward circumferential direction FC. The spinning rotor draws the blood into the channels 21 and impels the blood downstream, in the fluid flow direction F. As the rotor spins, the radial bearings 22 hold the rotor centered within the bore 55 of the housing and out of contact with the wall of the bore. The radial bearings 22 operate as hydrodynamic bearings. A small portion of the blood passing through the pump enters the pockets of the radial bearings, and encounters the sloping pocket surfaces. This interaction generates forces on the rotor directed radially inwardly, toward the axis.

A small portion of the blood flowing within bore 55 passes between the chamfer surfaces 30 of the rotor and the stop surface 56 of the casing. This blood enters into the pockets defined by thrust bearing surfaces 35. The thrust bearings also operate as hydrodynamic bearings. As the rotor turns, the blood contained in the pockets applies forces to the thrust bearing surfaces. These forces are directed approximately normal to the bearing surfaces. Thus, the forces are directed along vector V, approximately opposite to the normal vector X of each thrust bearing surface. The forces on the thrust bearing surfaces thus have components directed radially inwardly, toward axis R, and also have components directed in the downstream direction D.

As pointed out above, the rotor is subjected to thrust forces and pressure forces directed upstream. The downstream component of the forces on the thrust bearing surfaces helps to counteract these forces. Thus, the downstream component of the forces on the thrust bearing, together with the axial magnetic stiffness of the stator, prevents the rotor from moving upstream and keeps the rotor out of contact with the stop surface 56.

The downstream force component generated by the thrust bearings varies directly with the sine of the chamfer angle A and varies directly with the chamfer length L. In theory, the maximum downstream force component would be obtained at a chamfer angle of 90 degrees. However, such a chamfer angle would mean that the stop surface constitutes an abrupt step in diameter of the bore 55. By contrast, chamfer angles of about 20-45 degrees or less facilitate fluid flow through the bore and still provide adequate downstream force components. Moreover, the radially-directed force components from the thrust bearings mean that the thrust bearings act as additional radial bearings at the upstream end of the rotor. The thrust bearings thus help to stabilize the rotor and maintain it centered in the bore of the housing.

The forces applied to the thrust bearings are directly related to the area of the thrust bearings. Surprisingly, despite the relatively small area available for the thrust bearings on the chamfer surfaces of the vanes, the thrust bearings provide enough force to aid in keeping the rotor out of contact with the stop surface. The forces applied to the thrust bearings also vary directly with the rotational speed of the rotor. This means that the forces applied by the thrust bearings will be greatest when they are most needed.

Again, the chamfer surfaces 30, and thrust bearing surfaces 35, may decrease or eliminate the risk of the rotor body 20 contacting the stop surface 56. This may be particularly useful when operating the pump 10 at higher speeds and/or capacity. The chamfer surfaces 30 and thrust bearing surfaces 35 may also allow the pump 10 to be operated at higher rotational speeds than a comparable pump without thrust bearings, to provide a greater pressure differential, greater flow rate or both.

Figure 4:
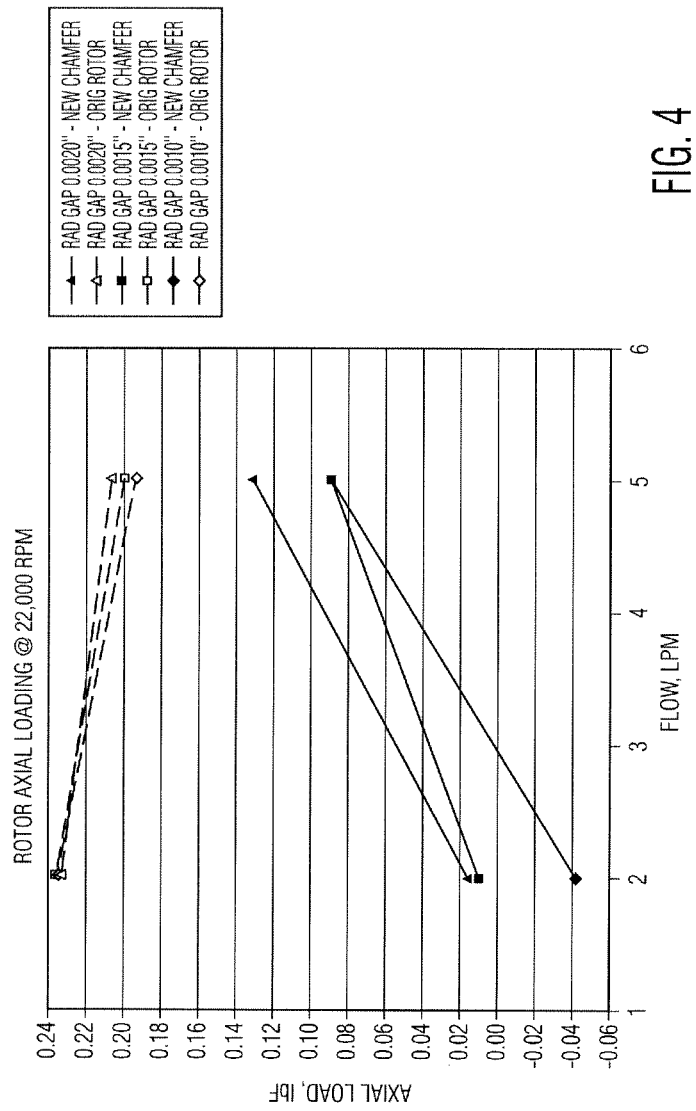
FIGS. 4 and 5 are graphical representations of data obtained representing performance of variations of the pump of FIG. 1, as compared to another pump.
Figure 5:
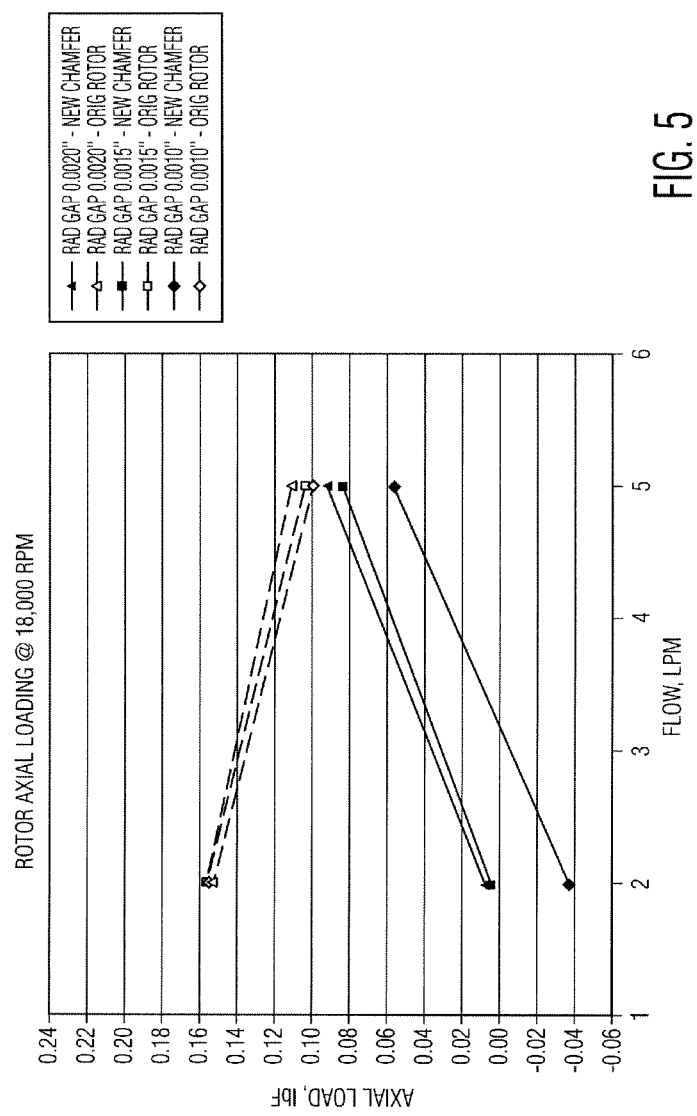

Computational simulation data has been obtained comparing a rotor generally in accordance with FIGS. 1-3 to a comparable rotor without the thrust bearings. FIGS. 4 and 5, for example, display the results of hydrodynamic simulations run on the pump 10 with thrust bearings as shown in FIGS. 1-3 (labeled "New Chamfer") versus an existing pump having a rotor of comparable configuration (labeled "Orig Rotor). The "Axial Load" (expressed in pounds force) represents the summation of all hydrodynamic and hydrostatic forces acting on the rotor. The axial load does not include magnetic forces associated with the axial magnetic stiffness of the stator. Rather, the axial load is the load which must be resisted by the axial magnetic stiffness of the stator to hold the rotor in place. Data is presented for combinations of rotors and casings with different radial gaps (labeled "Rad Gap"). The "radial gap" is one-half of the difference between the outside diameter of the rotor and the inside diameter of the bore in the casing. In these graphs, a positive axial load represents a load which tends to push the rotor upstream, whereas a negative axial load represents a net load in the downstream direction. The graphs show that the absolute value of axial loading on the rotor is significantly less for the pump with the thrust bearing, under all operating conditions studied.

Figure 6:
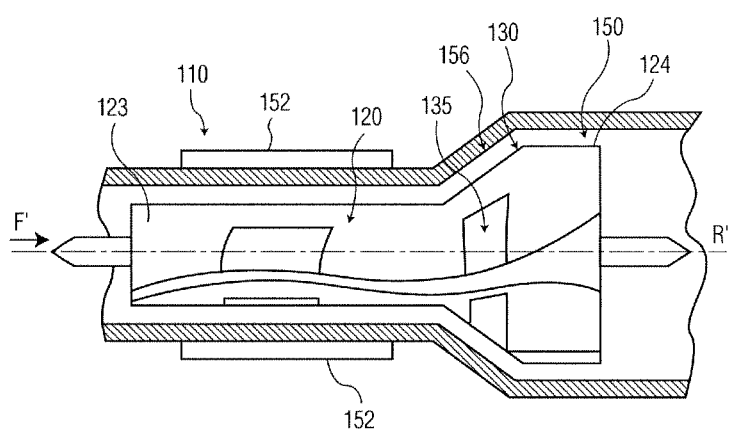
FIGS. 6 and 7 are diagrammatic sectional views depicting pumps in accordance with further embodiments of the invention.

A pump according to a further embodiment of the invention includes a rotor body 120 (FIG. 6) positioned within a casing 150. In this embodiment, the vanes of the rotor flare radially outwardly and define chamfer surfaces 130 near the downstream end 124 of rotor body 20 rather than at the upstream end 123. In this embodiment, the body 120 includes a substantially cylindrical body, but has a portion having a first diameter and a portion having a second diameter. The two portions are separated by the chamfer surfaces 130. Chamfer surfaces 130 are provided with thrust bearing surfaces 135, similar to thrust bearing surfaces of the embodiment discussed above. Casing 150 includes stop surface 156, which in this example is positioned downstream of the stator 152. Here again, the stop surface has a form of at least a portion of a surface of revolution about axis R'. This surface has a diameter which increases progressively in the downstream direction along the bore axis R'. Pump 110 operates in a similar fashion as the pump 10 discussed above with reference to FIGS. 1-3. Here again, rotor body 120 is prevented from migrating upstream by combined action of the magnet stiffness of stator 152 and the force generated by thrust surfaces 135.

Figure 7:
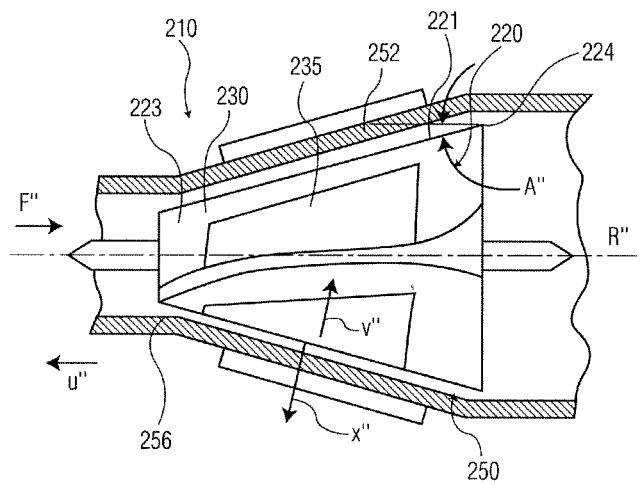

FIG. 7 illustrates yet another embodiment of a blood circulating pump 210. In this embodiment, the vanes of the rotor progressively increase in diameter along the length of the body. Thus, the main portion of rotor body 220 has a tapered peripheral surface 221 generally in the form of a surface of revolution about axis R" having progressively increasing diameter in the downstream direction. In the particular embodiment depicted, the peripheral surface 221 of the rotor main portion is a cone having a generatrix disposed at an angle A" to axis R". This peripheral surface is provided with bearing surfaces 235. The casing 250 includes a bore with an interior surface 256 which also has a diameter which increases progressively in the downstream direction along the axis R". The inwardly facing surface 256 is complementary to the outwardly facing peripheral surface 221 of the rotor. Thus, surface 256 may be a conical surface having a generatrix disposed at approximately the same angle A" to axis R". Also in this example, the stator 252 surrounds at least a portion of the interior surface 256 and tapered peripheral surface 221 of the rotor. In this embodiment, each bearing surface 235 has a normal vector X" with a positive, non-zero component in the upstream direction U" and also in the radially outward direction, away from axis R". The normal vector X" desirably also has a component in the circumferentially forward direction. Upon rotation of rotor 220 about axis R" in the forward direction, each bearing surface 235 will be subjected to forces directed along vector V", with both downstream and radially inward components. Thus, bearing surfaces 235 act as radial bearings to keep the rotor centered in the bore of the housing, and also act as thrust bearing surfaces to provide downstream forces on the rotor. Because the bearing surfaces 235 may be larger than the bearing surfaces 35 (FIGS. 1-3), the angle A" may be relatively small as, for example, a few degrees while still providing sufficient downstream force component.

The exemplary devices and uses herein focus on the use of the pump as a heart pump for the transfer of blood therethrough, for use in humans or other mammals in the event of heart disease or severe trauma. However, it is envisioned that other similar uses may be available for use on other animals or for other anatomical systems requiring assisted fluid flow.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A rotor for a blood circulating pump for the circulation of blood, the rotor comprising a magnetic, biocompatible body having an upstream end, a downstream end and an axis extending between the ends on which the rotor circumferentially rotates, the body including a plurality of vanes defining a plurality of channels therebetween, the rotor being constructed and arranged to impel blood downstream upon rotation of the rotor about the axis in a forward circumferential direction, the vanes having hydrodynamic thrust bearing surfaces, each such thrust bearing surface having a normal vector with non-zero components in the upstream and circumferentially forward directions and being constructed and arranged to apply a hydrodynamic force to the rotor with a component of the force in a downstream direction along the axis upon rotation of the rotor in the forward circumferential direction, wherein the vanes include chamfer surfaces generally in the form of portions of a conical surface of revolution about the axis having increasing diameter in the downstream direction, each of the chamfer surfaces including at least one hydrodynamic thrust bearing surface recessed relative to surrounding portions of the chamfer surfaces so that each thrust bearing surface is positioned completely on a particular chamfer surface and each thrust bearing surface defines a pocket in the chamfer surface, wherein the chamfered surfaces include a chamfer angle such that the chamfered surfaces are positioned at an angle relative to the axis and a generally cylindrical surface of revolution of the biocompatible body, the chamfer angle is in the range of about 20 degrees to less than about 45 degrees.

2. A rotor as claimed in claim 1, wherein the normal vector of each said hydrodynamic thrust bearing surface also has a non-zero component in a radially outward direction, away from the axis.

3. The rotor as claimed in claim 1, wherein the chamfer angle of the chamfered surfaces is about 30 degrees.

4. The rotor as claimed in claim 1, wherein the chamfered surfaces include a chamfer length, wherein the chamfer length is in the range of about 0.06 inches to about 0.1 inches.

5. The rotor as claimed in claim 4, wherein the chamfer length is about 0.08 inches.

6. A rotor as claimed in claim 1, wherein each said pocket in the chamfer surface has progressively increasing depth in the circumferentially forward direction.

7. A rotor as claimed in claim 6, wherein each said pocket has a circumferentially forward end open to one of said channels.

8. The rotor as claimed in claim 7, wherein the pocket defines a gap height, measured at the forward open end of the pocket, of about 0.0010 inches to about 0.0020 inches.

9. The rotor as claimed in claim 8, wherein the radial gap height is about 0.0015 inches.

10. A pump comprising a rotor as claimed in claim 1, and a casing having an interior bore having an axis, an upstream end, a downstream end, and a stop surface bounding the bore, the stop surface being substantially in the form of at least a portion of the surface of revolution and having a diameter increasing progressively in a downstream direction along the bore axis, the rotor being disposed within the casing with the upstream end of the rotor disposed adjacent the stop surface.

11. The rotor as claimed in claim 10, wherein the stop surface has a substantially reciprocal shape to the chamfer surfaces.

12. The rotor as claimed in claim 10, further comprising a stator disposed in proximity to the casing outside the bore, the stator including one or more electromagnetic coils for applying a magnetic field to the rotor so as to rotate the rotor about the axis.

13. An implantable blood circulating pump, the pump comprising:
(a) a casing having an interior bore having an axis, an upstream end, a downstream end, and a stop surface bounding the bore, the stop surface being substantially in the form of at least a portion of a conical surface of revolution about the bore axis having a diameter increasing progressively in a downstream direction along the bore axis;
(b) a rotor disposed within the bore, the rotor comprising a magnetic, biocompatible body including a plurality of vanes defining a plurality of channels therebetween, the rotor being constructed and arranged to impel blood downstream upon rotation of the rotor within the bore in a forward circumferential direction about the axis, the vanes having hydrodynamic thrust bearing surfaces, each such thrust bearing surface having a normal vector with non-zero components in the upstream and circumferentially forward directions and being constructed and arranged to apply a hydrodynamic force to the rotor with a component of the force in the downstream direction upon rotation of the rotor in the forward circumferential direction, wherein the vanes include chamfer surfaces generally in the form of portions of a conical surface of revolution about the axis having increasing diameter in the downstream direction, each thrust bearing surface is positioned completely on a particular chamfer surface and each thrust bearing surface defines a pocket in the chamfer surface, wherein the chamfered surfaces include a chamfer angle such that the chamfered surfaces are positioned at an angle relative to the axis and a generally cylindrical surface of revolution of the biocompatible body, the chamfer angle is in the range of about 20 degrees to less than about 45 degrees; and
(c) a stator disposed in proximity to the casing outside the bore, the stator including one or more electromagnetic coils for applying a magnetic field to the rotor so as to rotate the rotor about the axis.

14. The pump as claimed in claim 13, wherein the normal vector of each said hydrodynamic thrust bearing surface also has a non-zero component in a radially outward direction, away from the axis.

15. The pump as claimed in claim 14, wherein each hydrodynamic thrust bearing surface is recessed relative to surrounding portions of the chamfer surfaces so that each thrust bearing surface defines a pocket in the chamfer surface.

16. The pump as claimed in claim 15, wherein the stop surface has a substantially reciprocal shape to the chamfer surfaces.

* * * * *